United States Patent
Cardin

(10) Patent No.: US 10,849,600 B2
(45) Date of Patent: *Dec. 1, 2020

(54) BREATH CONDENSATE AND SALIVA ANALYSIS USING ORAL RINSE

(71) Applicant: Entech Instruments Inc., Simi Valley, CA (US)

(72) Inventor: Daniel B. Cardin, Simi Valley, CA (US)

(73) Assignee: Entech Instruments Inc., Simi Valley, CA (US)

(*) Notice: Subject to any disclaimer, the term of this patent is extended or adjusted under 35 U.S.C. 154(b) by 390 days.

This patent is subject to a terminal disclaimer.

(21) Appl. No.: 15/649,480

(22) Filed: Jul. 13, 2017

(65) Prior Publication Data

US 2017/0303900 A1 Oct. 26, 2017

Related U.S. Application Data

(63) Continuation-in-part of application No. 15/450,236, filed on Mar. 6, 2017, now Pat. No. 10,502,664.

(Continued)

(51) Int. Cl.
*A61B 10/00* (2006.01)
*G01N 33/497* (2006.01)
(Continued)

(52) U.S. Cl.
CPC .......... *A61B 10/00* (2013.01); *A61B 10/0051* (2013.01); *G01N 1/20* (2013.01);
(Continued)

(58) Field of Classification Search
CPC ................ A61B 10/00; A61B 10/0051; A61B 2010/0087; A61B 2217/005; G01N 30/06;
(Continued)

(56) References Cited

U.S. PATENT DOCUMENTS 4,170,901 A * 10/1979 Conkle ................ G01N 1/2273
219/535
4,213,326 A 7/1980 Brodasky
(Continued)

FOREIGN PATENT DOCUMENTS

CN 101793880 A 8/2010
CN 203324233 U 12/2013
(Continued)

OTHER PUBLICATIONS

Non-Final Office Action dated Feb. 7, 2019, for U.S. Appl. No. 15/450,236, filed Mar. 6, 2017, 15 pages.
(Continued)

*Primary Examiner* — Marrit Eyassu
(74) *Attorney, Agent, or Firm* — Kubota & Basol LLP

(57) ABSTRACT

A sample extraction device and a desorption device for use in gas chromatography (GC), gas chromatography-mass spectrometry (GCMS), liquid chromatography (LC), and/or liquid chromatography-mass spectrometry (LCMS) are disclosed. In some examples, the sample extraction device includes a lower chamber holding a sorbent. The sample extraction device can extract sample headspace gas from a sample vial by placing the sorbent inside the vial and creating a vacuum to increase recovery of low volatility compounds, for example. Once the sample has been collected, the sample extraction device can be inserted into a desorption device. The desorption device can control the flow of a carrier fluid (e.g., a liquid or a gas) through the sorbent containing the sample and into a pre-column and/or a primary column of a chemical analysis device for performing GC, GCMS, LC, LCMS, and/or some other chemical analysis process.

19 Claims, 8 Drawing Sheets

Related U.S. Application Data

(60) Provisional application No. 62/363,050, filed on Jul. 15, 2016, provisional application No. 62/305,468, filed on Mar. 8, 2016.

(51) Int. Cl.

| | | |
|---|---|---|
| *G01N 33/487* | (2006.01) | |
| *G01N 30/06* | (2006.01) | |
| *G01N 1/20* | (2006.01) | |
| *G01N 1/40* | (2006.01) | |
| *G01N 1/22* | (2006.01) | |
| G01N 30/00 | (2006.01) | |

(52) U.S. Cl.
CPC ........... *G01N 1/2226* (2013.01); *G01N 1/405* (2013.01); *G01N 30/06* (2013.01); *G01N 33/487* (2013.01); *G01N 33/497* (2013.01); *A61B 2010/0087* (2013.01); *A61B 2217/005* (2013.01); *G01N 2001/2229* (2013.01); *G01N 2001/2244* (2013.01); *G01N 2001/2276* (2013.01); *G01N 2001/4061* (2013.01); *G01N 2030/009* (2013.01); *G01N 2030/062* (2013.01)

(58) Field of Classification Search
CPC ........ G01N 1/405; G01N 1/2226; G01N 1/20; G01N 33/487; G01N 33/497; G01N 2030/062; G01N 2030/009; G01N 2001/4061; G01N 2001/2276; G01N 2001/2244; G01N 2001/2229
USPC ...................................................... 73/863.23
See application file for complete search history.

(56) References Cited

U.S. PATENT DOCUMENTS

| | | | |
|---|---|---|---|
| 4,849,179 A | 7/1989 | Reinhardt et al. | |
| 5,198,197 A * | 3/1993 | Clay | B01D 11/0203 210/634 |
| 5,347,844 A | 9/1994 | Grob et al. | |
| 5,363,707 A | 11/1994 | Augenblick et al. | |
| 5,496,741 A | 3/1996 | Pawliszyn | |
| 5,711,786 A | 1/1998 | Hinshaw | |
| 5,792,423 A | 8/1998 | Markelov | |
| 5,866,004 A * | 2/1999 | Houck | B01D 11/0203 210/136 |
| 5,900,532 A * | 5/1999 | Ikeda | G01N 33/0016 73/23.41 |
| 6,177,008 B1 | 1/2001 | Treiber et al. | |
| 6,186,012 B1 * | 2/2001 | Kenny | G01N 1/28 73/863.12 |
| 6,351,983 B1 | 3/2002 | Haas et al. | |
| 6,395,560 B1 | 5/2002 | Markelov | |
| 6,484,560 B1 | 11/2002 | Prest | |
| 6,649,403 B1 | 11/2003 | Mcdevitt et al. | |
| 6,662,626 B2 | 12/2003 | van der Maas | |
| 6,677,129 B1 | 1/2004 | Blume | |
| 6,770,246 B1 | 8/2004 | Husek | |
| 6,814,785 B2 | 11/2004 | Tipler et al. | |
| 7,329,393 B2 | 2/2008 | Backes et al. | |
| 7,464,614 B2 | 12/2008 | Harvey | |
| 7,568,401 B1 * | 8/2009 | Berends, Jr. | G01N 1/2214 73/863.21 |
| 7,700,045 B2 | 4/2010 | Skarping et al. | |
| 7,776,615 B2 | 8/2010 | Yuka et al. | |
| 8,182,768 B2 | 5/2012 | Tipler et al. | |
| 8,342,042 B2 | 1/2013 | Scott et al. | |
| 8,404,185 B2 | 3/2013 | Tipler et al. | |
| 8,465,700 B2 | 6/2013 | Huang | |
| 9,404,900 B2 | 8/2016 | Herman et al. | |
| 9,733,225 B2 | 8/2017 | Armstrong | |
| 2002/0144949 A1 | 10/2002 | Berger et al. | |
| 2004/0072375 A1 | 4/2004 | Gjerde et al. | |
| 2005/0014156 A1 | 1/2005 | Pawliszyn | |
| 2005/0019950 A1 | 1/2005 | Gierde et al. | |
| 2006/0073538 A1 * | 4/2006 | Konrad | A61B 10/0051 435/18 |
| 2006/0137432 A1 | 6/2006 | Kin et al. | |
| 2006/0286606 A1 | 12/2006 | Oliver | |
| 2007/0193871 A1 | 8/2007 | Wiseman et al. | |
| 2007/0284523 A1 | 12/2007 | May et al. | |
| 2008/0009761 A1 | 1/2008 | Acker et al. | |
| 2008/0064115 A1 * | 3/2008 | Hiramatsu | B01D 15/00 436/178 |
| 2008/0179252 A1 | 7/2008 | Sasano et al. | |
| 2011/0033949 A1 * | 2/2011 | Eum | G01N 1/4044 436/175 |
| 2011/0277563 A1 | 11/2011 | Scott et al. | |
| 2012/0160038 A1 | 6/2012 | Wells et al. | |
| 2012/0310113 A1 * | 12/2012 | Giddings | A61B 10/0051 600/570 |
| 2013/0017545 A1 | 1/2013 | Yong et al. | |
| 2014/0329705 A1 * | 11/2014 | Wong | C12Q 1/68 506/9 |
| 2014/0345365 A1 | 11/2014 | Aono et al. | |
| 2015/0075300 A1 | 3/2015 | Hankemeier et al. | |
| 2015/0276780 A1 | 10/2015 | Bremer et al. | |
| 2015/0364310 A1 | 12/2015 | Musselman | |
| 2017/0261408 A1 | 9/2017 | Cardin | |
| 2017/0284978 A1 | 10/2017 | Cardin | |
| 2018/0246071 A1 | 8/2018 | Cardin | |
| 2019/0274588 A1 | 9/2019 | Cardin | |
| 2020/0191686 A1 | 6/2020 | Cardin | |

FOREIGN PATENT DOCUMENTS

| | | | |
|---|---|---|---|
| CN | 104133031 A | 11/2014 | |
| CN | 105866272 A | 8/2016 | |
| CN | 106124255 A | 11/2016 | |
| CN | 107085046 A | 8/2017 | |
| EP | 0 572 968 A2 | 12/1993 | |
| EP | 2158469 A2 | 3/2010 | |
| EP | 2 469 261 A1 | 6/2012 | |
| EP | 3 040 721 A1 | 7/2016 | |
| JP | 10-185890 A | 7/1998 | |
| JP | 2002-328078 A | 11/2002 | |
| JP | 2015-197444 A | 11/2015 | |
| KR | 2004-0012068 A | 2/2004 | |
| SU | 817583 A1 | 3/1981 | |
| WO | WO-94/28409 A2 | 12/1994 | |
| WO | WO-2008/020416 A2 | 2/2008 | |
| WO | WO-2008020416 A2 * | 2/2008 | G01N 24/08 |
| WO | WO-2008/157074 A2 | 12/2008 | |
| WO | 2008/157074 A3 | 1/2010 | |
| WO | WO-2011031559 A1 * | 3/2011 | A47C 7/72 |
| WO | WO-2011/143349 A1 | 11/2011 | |
| WO | WO-2017/156005 A1 | 9/2017 | |
| WO | WO-2018/013946 A1 | 1/2018 | |
| WO | 2018/160757 A1 | 9/2018 | |

OTHER PUBLICATIONS

International Search Report dated Jun. 1, 2017, for PCT Application No. PCT/US2017/021167, seven pages.
International Search Report dated Sep. 14, 2017, for PCT Application No. PCT/US2017/042172, six pages.
International Search Report dated May 28, 2018, for PCT Application No. PCT/US2018/020313, six pages.
Corrected Notice of Allowance received for U.S. Appl. No. 15/450,236, dated Nov. 13, 2019, 2 pages.
Dyne et al. "A Novel Device for Capturing Breath Samples for Solvent Analysis", Science of the Total Environment, vol. 199, No. 1-2, 1997, pp. 83-89.
International Preliminary Report on Patentability received for PCT Patent Application No. PCT/US2017/042172, dated Jan. 24, 2019, 9 pages.
International Preliminary Report on Patentability received for PCT Patent Application No. PCT/US2018/020313, dated Sep. 12, 2019, 10 pages.

(56) References Cited

OTHER PUBLICATIONS

International Search Report and Written Opinion received for PCT Patent Application No. PCT/US2019/020995, dated Jun. 11, 2019, 12 pages.
Notice of Allowance received for U.S. Appl. No. 15/450,236, dated Jun. 20, 2019, 8 pages.
Restriction Requirement received for U.S. Appl. No. 15/908,491, dated Nov. 19, 2019, 7 pages.
Schubert et al. "C02-controlled Sampling of Alveolar Gas in Mechanically Ventilated Patients", J. Appl. Physiol., vol. 90, No. 2, 2001, pp. 486-492.
Non-Final Office Action received for U.S. Appl. No. 15/908,491, dated Mar. 23, 2020, 12 pages.

* cited by examiner

BREATH CONDENSATE AND SALIVA ANALYSIS USING ORAL RINSE

CROSS-REFERENCE TO RELATED APPLICATIONS

This application is a continuation-in-part of U.S. patent application Ser. No. 15/450,236, filed on Mar. 6, 2017, which claims the benefit of U.S. Provisional Patent Application No. 62/305,468, filed on Mar. 8, 2016, and claims benefit to U.S. Provisional Patent Application No. 62/363,050, filed on Jul. 15, 2016, the entire disclosures of which are incorporated herein by reference in their entirety for all intended purposes.

FIELD OF THE DISCLOSURE

This relates to a sample extraction device and, more particularly, to a sample extraction device for use in various chromatography techniques such as gas chromatography (GC), gas chromatography-mass spectrometry (GCMS), liquid chromatography (LC) and/or liquid chromatography-mass spectrometry (LCMS).

BACKGROUND OF THE DISCLOSURE

GC, GCMS, LC and LCMS are techniques of performing analysis of trace chemicals in a wide range of sample matrices. In some examples, these techniques can be used to study biological matrices such as breath, blood, and urine; to study trace chemicals in food, water, and air; to detect odors in foods, beverages, products, and water supplies; and/or to analyze pharmaceuticals dissolved in water.

In some examples, samples for GC, GCMS, LC, and LCMS can be prepared using solvent extraction, also known as liquid-liquid extraction. Solvent extraction can include transferring one or more solutes from a feed solution to a solvent to form an extract, which can then be analyzed by GC, GCMS, LC, LCMS, or other analytical techniques, for example. In some examples, headspace analysis can be another approach for sample preparation and cleanup. Headspace analysis can include capturing the headspace gas contained in a sample vial holding a liquid or solid sample, for example. In some examples, the liquid or solid sample can fully or partially evaporate into the headspace gas so that when the headspace gas is captured, some or all of the sample is captured in a gaseous state. In some circumstances, trace level components of the sample are transferred into the headspace, leaving the majority of the liquid or solid matrix behind. However, headspace analysis can traditionally suffer from poor sensitivity and limited volatility range due to the small gas phase sample size limitations of many techniques, the inability to concentrate or "enrich" the headspace compounds prior to instrumental analysis, and the inability to further extract chemicals out of the liquid or solid phase to enrich low volatility compounds. Thus, there exists a need for a device and method for quantitatively extracting samples for GC, GCMS, LC, or LCMS with improved sensitivity and volatility range.

SUMMARY OF THE DISCLOSURE

This disclosure relates to a sample extraction device and, more particularly, to a sample extraction device for use in various chromatography techniques such as gas chromatography (GC), gas chromatography-mass spectrometry (GCMS), liquid chromatography (LC) and/or liquid chromatography-mass spectrometry (LCMS). In some examples, the sample extraction device can be referred to as a Sorbent Pen. The sample extraction device can contain a sorbent configured to absorb or adsorb a sample. In some examples of the disclosure, the sample extraction device can be inserted into a sample vial to collect sample and/or headspace gas containing the sample. A vacuum can be drawn through an internal seal of the sample extraction device to facilitate rapid and thorough collection of the sample, for example. In some examples, the disclosed sample extraction techniques that occur under vacuum can be referred to as Vacuum-Assisted Sorbent Extraction, or VASE. In some examples, the sample collection device can be used at a higher pressure, such as atmospheric pressure, inside the sample vial or outside of the sample vial (e.g., to sample the air around the sample extraction device).

Once the sample has been extracted, the sample extraction device can be coupled to a chemical analysis device and chemical analysis (e.g., GC, GCMS, LC, or LCMS) can occur. The sample extraction device can allow the flow of a carrier fluid (e.g., a gas or a liquid) through a sorbent containing the sample, and into a pre-column and/or a primary column of a chemical analysis device configured to perform GC, GCMS, LC, LCMS, and/or some other sample analysis procedure.

DETAILED DESCRIPTION

In the following description, reference is made to the accompanying drawings which form a part hereof, and in which it is shown by way of illustration specific examples that can be practiced. It is to be understood that other examples can be used and structural changes can be made without departing from the scope of the examples of the disclosure.

This disclosure relates to a sample extraction device and, more particularly, to a sample extraction device for use in various chromatography techniques such as gas chromatography (GC), gas chromatography-mass spectrometry (GCMS), liquid chromatography (LC) and/or liquid chromatography-mass spectrometry (LCMS). In some examples, the sample extraction device can be referred to as a Sorbent Pen. The sample extraction device can contain a sorbent configured to absorb or adsorb a sample. In some examples of the disclosure, the sample extraction device can be inserted into a sample vial to collect sample and/or headspace gas containing the sample. A vacuum can be drawn through an internal seal of the sample extraction device to facilitate rapid and thorough collection of the sample, for example. In some examples, the disclosed sample extraction techniques that occur under vacuum can be referred to as Vacuum-Assisted Sorbent Extraction, or VASE. In some examples, the sample collection device can be used at a higher pressure, such as atmospheric pressure, inside the sample vial or outside of the sample vial (e.g., to sample the air around the sample extraction device).

Once the sample has been extracted, the sample extraction device can be coupled to a chemical analysis device and chemical analysis (e.g., GC, GCMS, LC, or LCMS) can occur. The sample extraction device can allow the flow of a carrier fluid (e.g., a gas or a liquid) through a sorbent containing the sample, and into a pre-column and/or a primary column of a chemical analysis device configured to perform GC, GCMS, LC, LCMS, and/or some other sample analysis procedure.

Figure 1A:
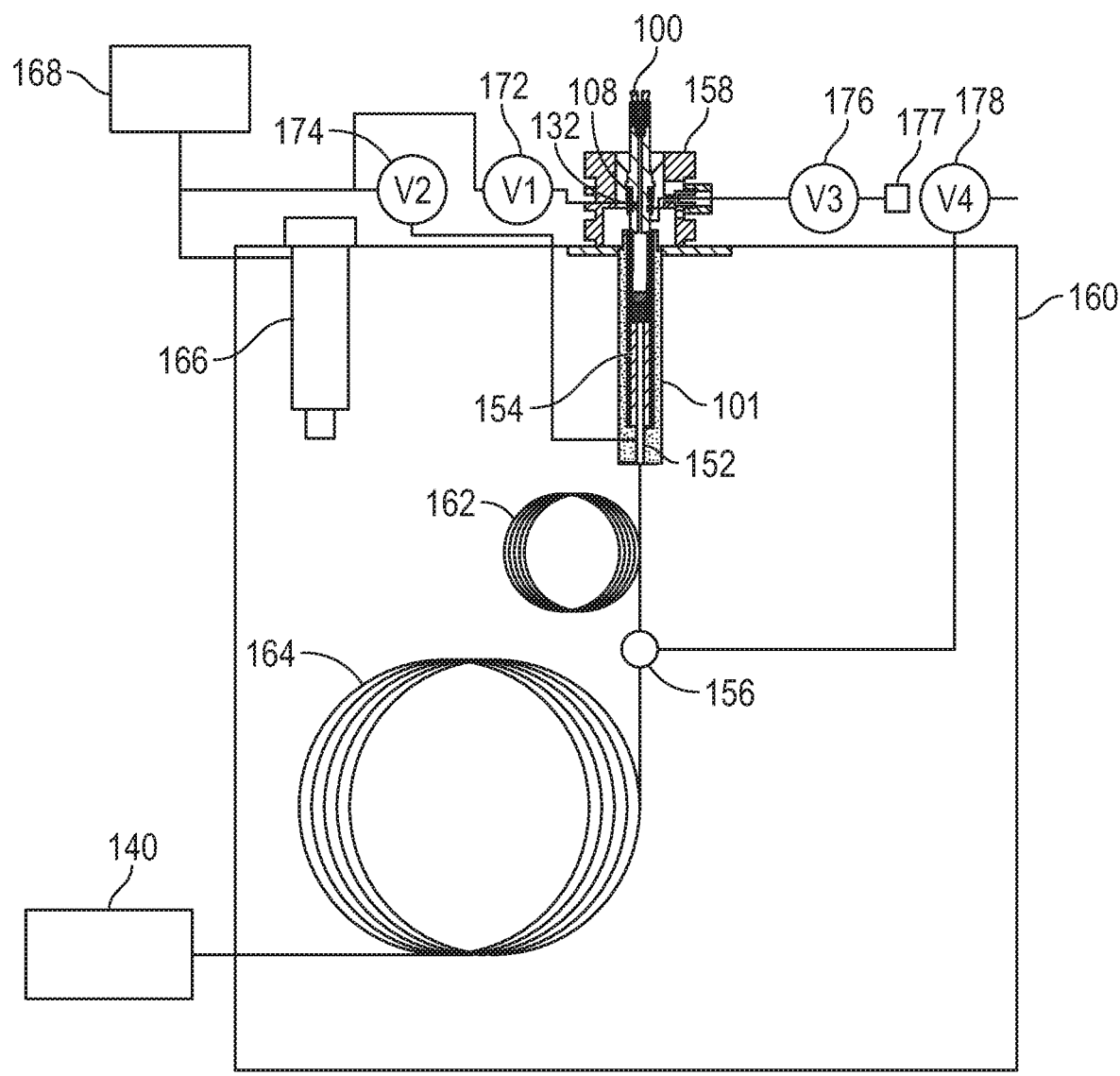
FIG. 1A illustrates an exemplary sample extraction device, an exemplary desorption device and an exemplary chemical analysis device for conducting chemical analysis according to examples of the disclosure.

FIG. 1A illustrates an exemplary sample extraction device 100 and an exemplary chemical analysis device 160 and detector 140 for conducting chemical analysis according to examples of the disclosure. In some examples, chemical analysis device 160 and detector 140 can correspond to a chromatograph configured to perform gas chromatography (GC), gas chromatography-mass spectrometry (GCMS), liquid chromatography (LC), liquid chromatography-mass spectrometry (LCMS) or some other form of chemical analysis, including other forms of chromatography (e.g., detector 140 can be a mass spectrometer for detecting samples passing through the chemical analysis device 160, such as a quadrupole mass spectrometer). The sample extraction device 100 can house a sample that was previously collected in a sample collection process, as will be described below with reference to FIGS. 2-3, for example.

In some examples, the chemical analysis device 160 can desorb sample from the sample extraction device 100 using a thermal desorber configuration that will now be described. Specifically, in some examples, the chemical analysis device 160 can include divert vent 156, pre-column 162, primary column 164, injector 166, pressure controller 168, thermal desorption device 101 into which sample extraction device 100 can be inserted for desorbing sample into chemical analysis device 160, and a plurality of valves 172-178. Additionally, detector 140 can be included in chemical analysis device 160 as an integrated part, for example. In some examples, injector 166 can be a capped-off GC injector.

The desorption device 101 can be made of stainless steel and can optionally be lined with ceramic, and can include a replaceable liner 154 and heat sink 158. The replaceable liner 154 can improve transfer of sample from the sample extraction device 100 to the pre-column 162 and primary column 164 of chemical analysis device 160 without (or with minimal) chemical reactions, for example. Further, liner 154 can include channel 152 to fluidly couple the sample extraction device 100 to the chemical analysis device 160. In some examples, heat sink 158 can protect rubber seals 108 between the sample extraction device 100 and the desorption device 101 from excessive heat exposure and/or chemical outgassing. As an example, the rubber seals 108 can be included in the sample extraction device, as will be described below with reference to FIGS. 2A-2C.

In some examples, during the chemical analysis process (e.g., GC, GCMS, LC, or LCMS), the first valve 172 can control flow of a carrier fluid from pressure controller 168 through sorbent inside sample extraction device 100 for transfer of sample from the sample extraction device 100 to the pre-column 162 and primary column 164. The first valve 172 can be fluidly coupled to the sample extraction device 100 by way of port 132 of the sample extraction device 100, for example. Depending on the chemical analysis procedure and in the disclosed configuration, the carrier fluid can be a gas (e.g., for GC or GCMS), though it is understood that in some configurations, the carrier fluid can be a liquid (e.g., for LC or LCMS). The second valve 174 can control the flow of fluid around (e.g., bypassing) the sample extraction device 100 into channel 152 during preheating and can also be used to check for leaks between the sample extraction device 100 and desorption device 101, for example. In some examples, the third valve 176 can control flow of fluid (flowing into sample extraction device 100 via the first valve 172) directly out a split vent 177 to precisely and reproducibly reduce the amount of sample transferred to the pre-column 162 and primary column 164 and/or to increase sample injection rates into the chemical analysis device 160. The fourth valve 178 can control flow of fluid out from a divert vent 156 downstream of the pre-column 162 for either high flow pre-column enrichment without splitting, or back-flushing to prevent contamination of the primary column 164 with heavier contaminants, for example.

Upon desorption of the sample, the sample can pass through the pre-column 162 and the column 164 at a rate controlled by controller 168 by way of controlling the pressure of carrier gas. As the sample flows through the pre-column 162 and column 164, various compounds of the sample can move at different rates depending on compound mass, for example. In some examples, the sample can exit column 164 to enter the detector device 140, which can be used to identify the relative concentrations of compounds present in the sample based on time of arrival at the detector device 140 and by the mass fragmentation pattern of the compounds when using a mass spectrometer. In this way, the composition of the sample can be determined.

Figure 1B:
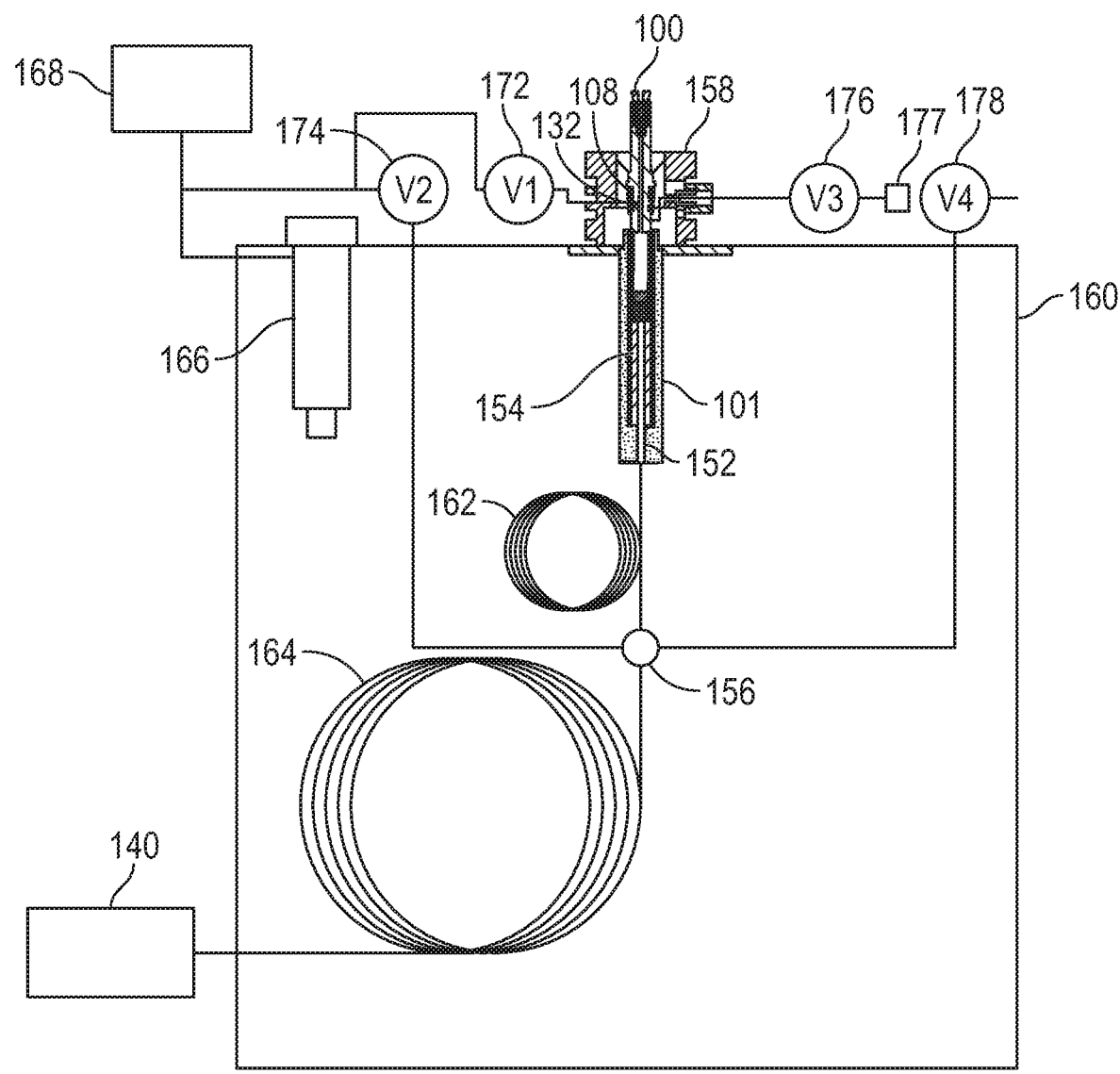
FIG. 1B illustrates an exemplary sample extraction device, an exemplary desorption device and an exemplary chemical analysis device for conducting chemical analysis according to examples of the disclosure.

FIG. 1B illustrates an exemplary sample extraction device 100, an exemplary desorption device 101 and an exemplary chemical analysis device 160 for conducting chemical analysis according to examples of the disclosure. The sample extraction device 100 and chemical analysis device 160 illustrated in FIG. 1B can include the same or similar components in the same or similar arrangements as those illustrated in FIG. 1A, for example. The chemical analysis device 160 illustrated in FIG. 1B can be substantially the same as the chemical analysis device illustrated in FIG. 1A with the modification that the V2 bypass 174 can be connected at the same point as divert vent 156, after the pre-column 162. In this configuration, the adsorbent can be pre-heated longer under "no-flow" so that desorption can occur faster, for example. Additionally, in some examples, as the gasses above the adsorbent preheat and expand, they can push the compounds away from the adsorbent, rather than allow compounds to diffuse further into the adsorbent during the preheating process. Accordingly, injection rates can be improved while also reducing the potential for carryover, for example.

Figure 1C:
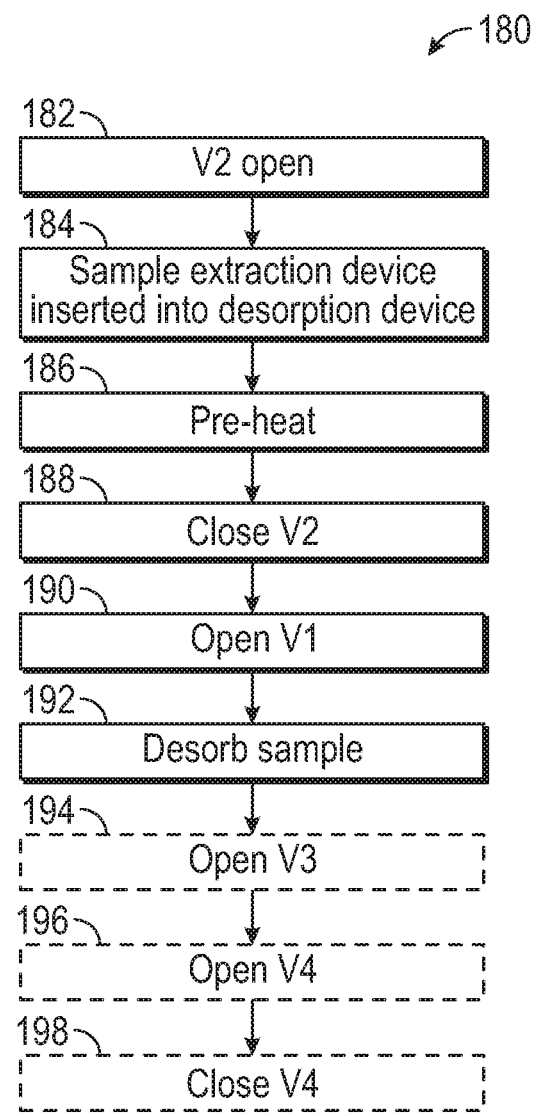
FIG. 1C illustrates an exemplary process for performing a chemical analysis procedure using a sample extraction device, desorption device, chemical analysis device, and detector according to examples of the disclosure.

FIG. 1C illustrates an exemplary process 180 for performing a chemical analysis procedure using sample extraction device 100, desorption device 101, chemical analysis device 160, and detector 140 according to examples of the disclosure. As an example, the chemical analysis process can be GCMS. To perform GCMS, the pressure controller 168 can supply a carrier gas, such as helium, nitrogen, or some other inert or non-reactive gas, which can flow through sorbent inside sample extraction device 100 and into pre-column 162 to facilitate sample extraction from the sorbent.

Initially, in step 182, the second valve 174 can be open, for example. In some examples, the sample extraction device 100 can be inserted into the desorption device 101 in step 184 while second valve 174 is open. Next, in step 186, a pre-heat can occur while second valve 174 is open. In some examples, the pre-heat can take zero to three minutes, though other lengths of time are possible. After the pre-heat, the second valve 174 can be closed in step 188 and the first valve 172, which can be fluidly coupled to the sample extraction device 100 by way of port 132 of the sample extraction device 100, can be opened in step 190. The closing of second valve 174 and the opening of first valve 172 can cause the desorption of the sample in step 192, for example. In some examples, at step 194, the third valve 176 can be opened to optionally perform a split injection. Performing a split injection can precisely and reproducibly reduce the amount of sample transferred to the column and increase injection rates, for example. In some examples, the third valve 176 is left open and the fourth valve 178 is opened in step 196 to improve transfer of heavy sample chemicals to the pre-column 162 while excess gas flows out from the fourth valve 178. Alternatively, in some examples, the third valve 176 can be left closed during sample desorption steps 192-196 to achieve complete transfer of heavy compounds into the pre-column 162. After desorption, if the fourth valve 178 had been opened in step 196, it can be closed in step 198, for example. The third valve 176 can open or remain open to remove any residual sample left in the sample extraction device 100 during a bake out process to clean the sample extraction device 100 for reuse in another sample analysis. In some examples, sample extraction device 100 can be reused hundreds of times in this way.

Figure 2A:
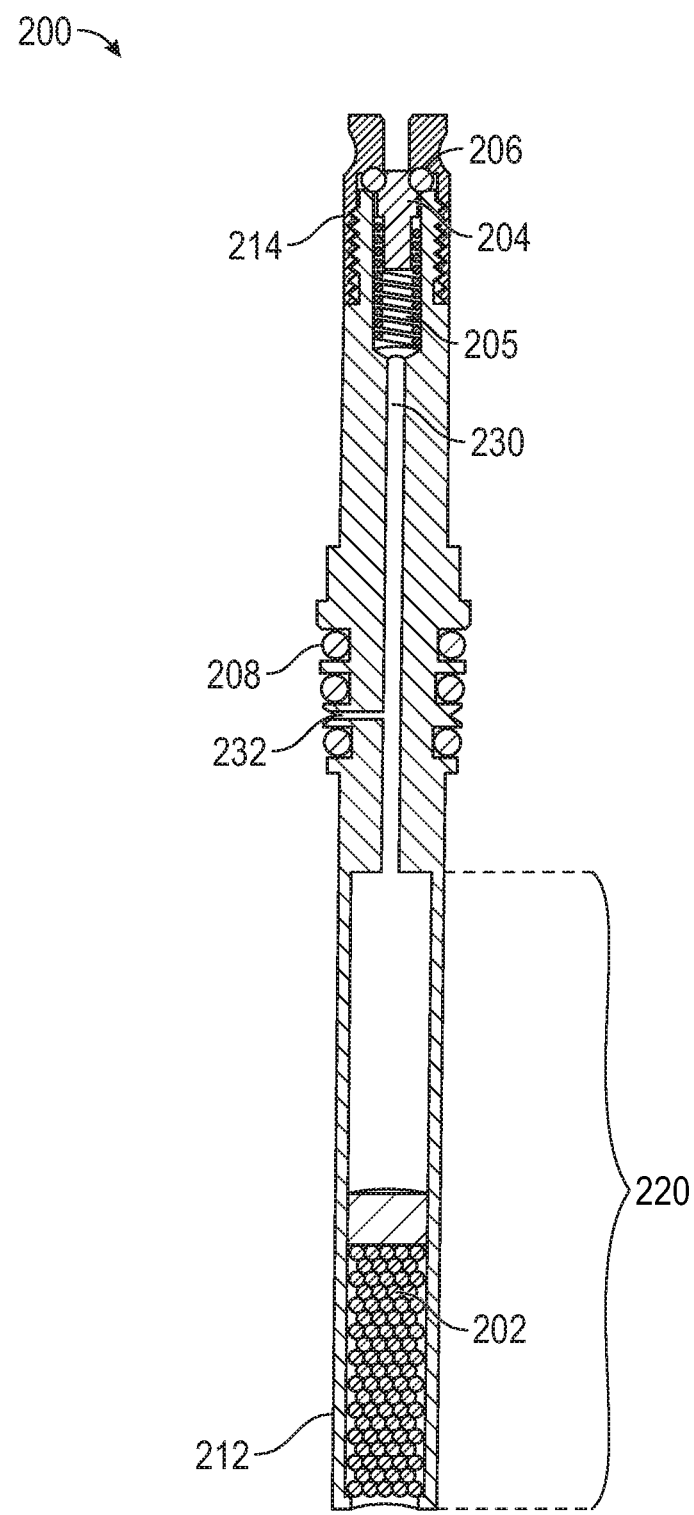
FIG. 2A illustrates an exemplary sample extraction device according to examples of the disclosure.

FIG. 2A illustrates an exemplary sample extraction device 200 according to examples of the disclosure. In some examples, sample extraction device 200 can correspond to sample extraction device 100 in FIGS. 1A-1C, and can be used for chemical analysis in a manner similar to that described with respect to FIGS. 1A-1C. As an example, sample extraction device 200 can have a diameter between $\frac{1}{32}$ in. and $\frac{3}{8}$ in. (e.g., the external or internal diameter of the sample extraction device); in some examples, the diameter of sample extraction device 200 can be as small as the diameters of the capillary columns (e.g., pre-column 162 and/or column 164) in the chemical analysis device. In some examples, other dimensions are possible. Sample extraction device 200 can comprise a tube-like structure, for example, that includes various channels and/or cavities as will be described below. In some examples, sample extraction device 200 can be fabricated from stainless steel or another suitable material (e.g., a material that is substantially inert). All or part of the surface of sample extraction device 200 can be coated with a chemical vapor deposition (CVD)-deposited ceramic to increase the inertness of the sample extraction device 200, for example. Other coatings that similarly increase the inertness of the sample extraction device 200 can similarly be used.

Sample extraction device 200 can include lower cavity 220. In some examples, the lower cavity 220 can contain a sorbent 202, which can be, for example, an adsorbent or an absorbent. The sorbent can be Tenax TA, Tenax/Carboxen, a short piece of 0.53 mm ID porous layer open tubular (PLOT) column ranging in composition from polydimethylsiloxane (PDMS), PLOT Q, and/or Carboxen, or some other sorbent that can be chosen based on the sample(s) to be collected by the sample collection device 200, for example. As will be described below, in some examples, sorbent 202 can be selected to collect a sample for analysis. In some examples, the sorbent 202 can be located towards an extraction end 212 of the sample extraction device 200. That is to say, sorbent 202 can be closer to the extraction end 212 of the sample extraction device 200 than it is to a valve end 214 of the sample extraction device. Extraction end 212 of the sample extraction device 200 can be open to the environment of the sample extraction device such that the sample being collected can enter lower cavity 220, and can adsorb or absorb to sorbent 202, as will be described in more detail below.

At the valve end 214 of the sample extraction device 200 (e.g., opposite extraction end 212 of the sample extraction device 200), the sample extraction device 200 can include a sealing plunger 204, a spring 205, and an internal seal 206, for example. The internal seal 206 can be a fluoroelastomer seal, a perfluoroelastomer seal, or any other suitable seal, for example. In some examples, sealing plunger 204 and internal seal 206 can selectively restrict fluid (e.g., gas, liquid, etc.) flow through internal channel 230 between sealing plunger 204/internal seal 206 and lower cavity 220/sorbent 202. For example, when sealing plunger 204 is pressed up against seal 206, fluid flow through sample extraction device 200 can be restricted, and when sealing plunger 204 is moved away or otherwise separated from seal 206, fluid flow through sample extraction device 200 may be unrestricted. In some examples, sealing plunger 204 can be tensioned via spring 205 against seal 206 such that in a default configuration, sealing plunger 204 can be pressed up against seal 206 and fluid flow through sample extraction device 200 can be restricted. In some examples, spring 205 can be fabricated from a non-reactive material, such as 316 stainless steel coated with a ceramic material using a chemical vapor deposition (CVD) process. Fluid flow (e.g., air being drawn into a vacuum source) through sample extraction device 200 can be allowed by causing sealing plunger 204 to move away from seal 206 (e.g., via mechanical means such as a pin from above, or other means). For example, a vacuum source can be coupled to the sample extraction device 100 at the valve end 214 to open sealing plunger 204 and draw a vacuum through sealing plunger 204, an internal channel 230, and lower cavity 220. Additionally, in some examples, sealing plunger 204 can remain open (e.g., during continuous vacuum evacuation) to evaporate unwanted matrix, such as water or alcohol, from the sample through sorbent 202.

As an example, during a sample extraction process in which a sample can be collected in sample extraction device 200, as will be described in more detail below, a vacuum can be drawn through sealing plunger 204, internal channel 230 and lower cavity 220 to facilitate sample collection by sorbent 202 in lower cavity 220. In some examples, after the sample has been collected by sample extraction device 200, the sealing plunger 204 can be opened to release the vacuum. However, releasing the vacuum by opening sealing plunger 204 can cause air to be pushed through sorbent 202. Thus, in some examples, the vacuum is not released via sealing plunger 204—rather, the sample extraction device 200 can simply be removed from the environment containing the sample (e.g., a sample vial) without releasing the vacuum, which can prevent air from entering the sorbent 202 in the reverse direction to prevent backflushing of the sorbent 202 which can cause loss of adsorbed/absorbed compounds. When, at a later time, the sample extraction device 200 is inserted into desorption device 101, sealing plunger 204 can be depressed to open the top of the valve using a restrictor on the outlet, for example. In some examples, this process can slowly purge helium from the chemical analysis device 160 over a time period of 0 to 2 minutes to eliminate air from the sample extraction device 200. In this way, excess water vapor and other matrix chemicals such as Ethanol can be forward purged before back desorption into chemical analysis device 160, for example. Additionally, in some examples, after the sample has been collected by the sample extraction device 200, the sealing plunger 204 can be remain closed (e.g., as it can be during sample collection) and can isolate the sample from the environment, allowing the sample to be stored in the sample extraction device 200 between extraction and analysis. For example, spring 205 can cause the sealing plunger 204 to remain closed in the absence of a mechanical force to open sealing plunger 204. During storage, the sample extraction device 200 can be kept in an isolation sleeve to avoid contaminating the sample. Subsequently, in some examples, during the chemical analysis process, a carrier fluid can be drawn through sealing plunger 204, into internal channel 230 and lower cavity 220, and into chemical analysis device 160, allowing for rapid desorption of the sample from sorbent 202 into the chemical analysis device 160. Additionally or alternatively, in some examples, during the chemical analysis process, the carrier fluid can be drawn through port 232 (e.g., instead of through sealing plunger 204), into internal channel 230 and lower cavity 220, and into chemical analysis device 160. In some examples, port 232 can be a channel in fluid communication with lower cavity 220 and the outside of sample extraction device 200. Preferably, the open end of port 232 can be located between external seals 208 so that port 232 can be sealed when the sample extraction device 100 is sealed against another object (e.g., a desorption device or sample vial), for example. In some examples, other locations on sample extraction device 200 are possible.

The sample extraction device 200 can further include one or more external seals 208, for example. The external seals 208 can be made of an elastomeric material and can be fluoroelastomer seals or perfluoroelastomer seals. In some examples, the external seals 208 can be Viton™ seals or other suitable seals. The external seals 208 can be located externally on sample extraction device 200 between ends 212 and 214. The external seals 208 can include one or more gaskets or o-rings fitted around the outside of the sample extraction device 200, for example. In some examples, the external seals 208 can be used to form a seal between sample extraction device 200 and a sample vial into which sample extraction device 200 can be inserted during a sample extraction process (which will be described with reference to FIG. 2B), and/or to form a seal between sample extraction device 200 and desorption device 101 into which sample extraction device 200 can be inserted during a sample desorption process (as described previously).

Figure 2B:
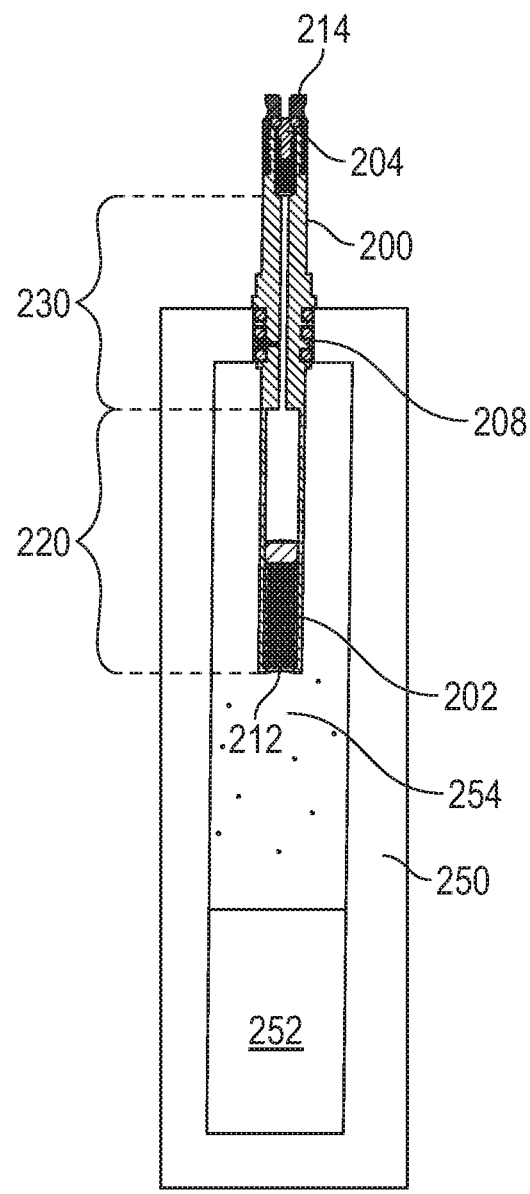
FIG. 2B illustrates an exemplary sample extraction device extracting a sample from a sample vial according to examples of the disclosure.

FIG. 2B illustrates an exemplary manner of extracting a sample from a sample vial 250 that includes sample 252 using sample extraction device 200 according to examples of the disclosure. In some examples, sample vial 250 can include a wall with a void into which sample extraction device 200 can be inserted, as shown (e.g., partially inserted into sample vial 250 such that extraction end 212 of sample extraction device 200 is inside sample vial 250, and valve end 214 of sample extraction device 200 remains outside of sample vial 250). Insertion of sample extraction device 200 into sample vial 250 can create a seal, at external seals 208, between sample extraction device 200 and sample vial 250 such that vacuum can be maintained inside sample vial 250 while sample extraction device 200 is inserted into sample vial 250. Sample vial 250 can contain a sample 252 and headspace gas 254, for example. Headspace gas 254 can include one or more compounds evaporated from sample 252. In some examples, sample 252 can be a liquid sample or a solid sample. Sample extraction device 200, seals 208, sample vial 250 and/or sample 252 can be configured such that when sample extraction device 200 is inserted into sample vial and sealed against sample vial 250, extraction end 212 of sample extraction device 200 can be positioned within headspace gas 254, above sample 252 (e.g., not positioned inside sample 252).

In some examples, while the sample extraction device 200 is inserted into sample vial 250, a vacuum can be pulled in sample vial 250 through the sample extraction device 200 by way of internal sealing plunger 204 (e.g., vacuum can be pulled through internal sealing plunger 204, internal channel 230 and lower cavity 220 containing sorbent 202). By pulling the vacuum through the sample extraction device 200 in this way, the evacuated headspace gas 254—which, in some examples, can include the sample of interest—can be absorbed or adsorbed by sorbent 202 in sample extraction device 200, as opposed to being lost as a result of by pulling vacuum in some other way (e.g., through a separate opening of the sample vial 250). In some examples, most (e.g., 99 percent or more) of the sample 252 can be in the solid or liquid phase when the vacuum is drawn, meaning the vacuum can mostly draw air, rather than evaporated sample, through sorbent 202. Thus, in some examples, it can be beneficial to draw vacuum via sample extraction device 200, remove the vacuum source, and leave extraction device 200 inside sample vial 250 in the vacuum-drawn state for a period of time to collect sample 252 in sorbent 202, as will be described in more detail below. The sample extraction device 200 can continue to hold the vacuum after the vacuum source is released, as previously described. During this time, the sample can continue to enter the gas phase and be collected by sorbent 202, as will now be described.

A vacuum source can pull the vacuum through the sample extraction device 200 for about 10-60 seconds, for example. The external seals 208 and internal seal 204 of the sample extraction device 200 can hold the vacuum even after the vacuum source has been removed. In some examples, the reduced pressure inside sample vial 250 can cause the volatile and semi-volatile chemicals within sample 252 to enter the gas phase more quickly, allowing for faster sample 252 extraction into sorbent 202 compared to collection of sample 252 at higher pressures. Specifically, once under vacuum, sample 252 can, via diffusion, find its way to sorbent 202. Many compounds can be more than 99% in the liquid or solid phase while the vacuum is being drawn and later enter the gas phase under the vacuum held by sample extraction device 200, for example. Once in the gas phase, the sample can enter the sample extraction device 200 and remain trapped by the sorbent 202. In some examples, the sample extraction device 200 can remain in the sample vial 250 holding a vacuum and extracting sample for anywhere from a few minutes to several days (e.g., 10 minutes to 1-2 days). The evaporation and collection of the sample can occur more quickly under vacuum than it would under atmospheric or other elevated pressures. Additionally, in some examples, sample extraction can be performed at elevated temperatures (e.g., 25° C. or 100° C.) to further improve extraction times. Such ability to extract sample 252 using sample extraction device 200 under vacuum for extended periods of time can allow significant sample 252 to build up in sorbent 202, which can allow sample extraction device 200 to collect, and subsequent chemical analysis processes to detect, sufficient amounts of even very low-level compounds in sample 252.

A number of factors can be considered in selecting extraction temperature and extraction time for a given sample. For example, some compounds have a low vapor pressure and a high boiling point and may be extracted at a higher temperature and/or for a longer time than compounds with a higher vapor pressure and a lower boiling point. In some examples, "exhaustive extraction" can be performed in which the vacuum is held in the sample vial 250 and extraction is allowed to occur until all volatile chemicals have been extracted from sample 252. "Exhaustive extraction" can be highly reproducible because the liquid or solid sample 252 can be weighed prior to extraction, and several trials can be prepared using the same weight of sample.

Extracting sample under vacuum using sample extraction device 200 can have several advantages. For example, vacuum extraction performed over a long integration time can better recover low-volatility compounds than possible by other methods. Additionally, the diffusive sample extraction process disclosed herein (i.e., extracting sample 252 under vacuum conditions) can improve recovery of heavy compounds (e.g., improved ability to desorb those compounds from sorbent 202 into the chemical analysis device or otherwise) due to reduced channeling into the sorbent 202, as compared to methods that rely on a carrier gas to deliver the sample to a sorbent bed. Additionally, performing sample extraction under vacuum as described (e.g., such that sample 252 has transitioned to the gas phase and is under vacuum) can allow molecules of sample to find the extraction end 212 of sample extraction device 200 (and thus sorbent 202) much faster than they would otherwise in non-vacuum conditions, increasing the rate of extraction, due to reduced gas phase collisions resulting in faster net diffusion rates in the sample vial 250. In some examples, the vacuum extraction of the disclosure can allow recovery of heavier compounds without applying heat during the sample extraction process, allowing natural and biological samples to be analyzed without breakdown of the sample, which can produce artifacts that were not in the original sample. Samples such as foods, beverages, blood, urine, breath condensate, and other samples that may not tolerate elevated temperatures can be sampled by vacuum extraction at room temperature or another non-elevated temperature, for example.

In some examples, the sample collected using the vacuum-assisted extraction techniques and sample extraction device 200 of the disclosure can remain captured towards the outermost edge of the sorbent 202 (i.e., proximate to the edge of sorbent 202 directly exposed to sample 252 at the extraction end 212 of the sample extraction device 200), rather than being driven deep into sorbent 202 due to dynamic extraction of sample pulled into sorbent 202 via gas flow. This tendency of the sample to remain captured towards the outermost edge of sorbent 202 can cause the sample to be desorbed into the desorption device 101 and/or chemical analysis device 160 more rapidly, as compared to a sample that is more evenly distributed through sorbent 202, for example. Further, this tendency can ensure more complete desorption of sample/compounds from sorbent 202, making it easier to reuse the sample extraction device 200 without risk of cross-contamination and/or carryover between uses. In some examples, the tendency of the sample to collect at the opening of the extraction end 212 of the sample extraction device 200 can keep the sample extraction device 200 cleaner, preventing thermal breakdown of the sample during desorption, thus increasing the number of reuses of the sample extraction device 200. Lastly, the sample extraction device 200 can hold large amounts of sorbent 202, thus reducing analytical variability even with moderate matrix-related affinity differences of sample compounds to the liquid or solid sample 252.

While optimal sample extraction may be performed under vacuum or lower-pressure conditions, in some examples, passive sample extraction can be performed using sample extraction device 200 in non-vacuum conditions inside sample vial 250, and can even be performed outside of the sample vial 250 to sample air, for example. Some of the sample extraction techniques of this disclosure that utilize sample extraction device 200 can occur without the use of solvents, making the disclosed extraction techniques "green" (e.g., environmentally friendly).

Once the sample 252 is collected in sorbent 202 inside sample extraction device 200, chemical analysis (e.g., GC, GC-MS, or LC) can be performed to determine the composition of the sample, as described herein, for example. As described above, the sample extraction techniques of the disclosure can occur "off-line" from the chemical analysis device 160 (e.g., performed outside and independent of the chemical analysis device 160), thus making sample extraction time independent of the time it takes to analyze the sample in the chemical analysis device 160. Therefore, sample preparation can occur remotely from the chemical analysis device 160, allowing for longer extraction times as needed and for the extraction and analysis to occur in different locations as needed. This flexibility in when and where extraction can occur can allow extraction to be optimized, thus improving the sensitivity and versatility of the sample extraction device 200, for example. Additionally, in some examples, the sample collected by sorbent 202 can be stored in the sample extraction device 200 for some time before analysis occurs.

Figure 2C:
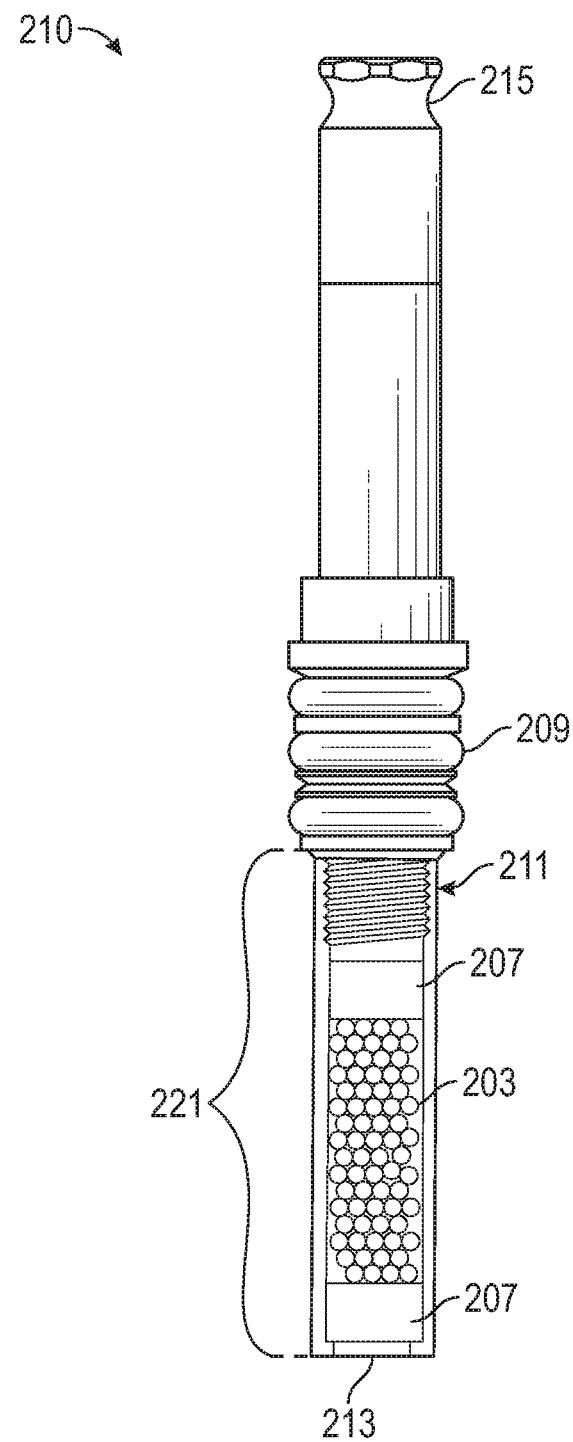
FIG. 2C illustrates another exemplary sample extraction device according to examples of the disclosure.

FIG. 2C illustrates another exemplary sample extraction device 210 according to examples of the disclosure. In some examples, sample extraction device 210 can be similar to sample extraction device 200 and can correspond to sample extraction device 100 in FIG. 1A to be used in a chemical analysis process similar to that described with respect to FIGS. 1A-1C. Sample extraction device 210 can include similar components to sample extraction device 200, such as external seal 209, lower cavity 221 with sorbent 203, extraction end 213, and a valve end 215, and can include various components of sample extraction device 200 not illustrated in FIG. 2C (e.g., sealing plunger 204 for pulling vacuum and/or selectively allowing solvent flow through the sample extraction device 210, spring 205, and internal seal 206), except as otherwise described here. In some examples, sample extraction device 210 can be used to extract samples that require LC or LCMS because they are not stable on a GC or GCMS column, and/or to extract samples that are better recovered using a solvent, rather than via thermal desorption prior to GC or GCMS. Accordingly, sample extraction device 210 can be used when sample from sample extraction device 210 is to be recovered using a solvent, whether for GC, GCMS, LC, and/or LCMS, for example. Because sample extraction device 210 can be used in conjunction with solvent, as described above, sorbent 203 can be a solvent-compatible sorbent.

In addition to components in common with sample extraction device 200, sample extraction device 210 can include threads 211 via which lower cavity 221 (including sorbent 203) can be attached to the remainder of the sample extraction device 210, and/or sorbent retention means 207, for example. In some examples, sorbent retention means 207 can be one or more screens, frits, or seals between which sorbent 203 can be contained in lower cavity 221, and which can confine sorbent 203 within lower cavity 221 such that sorbent 203 will not be expelled from sample extraction device 210 during solvent-extraction of the sample from the sample extraction device 210. As such, sorbent retention means 207 can be solvent-transmissive but not sorbent-transmissive. After sample extraction from sorbent 203 using a solvent (e.g., after the sample has been extracted for analysis by GC, GCMS, LC, and/or LCMS), the lower cavity 221 (including sorbent 203) can be removed for solvent extraction by decoupling the lower cavity 221 from the rest of the sample extraction device 210 at the threads 211. Solvent extraction can be conducted manually or in an automated manner, for example. In some examples, automated extraction can occur simultaneously with or sequentially with GC, GCMS, LC, and/or LCMS analysis.

Figure 3:
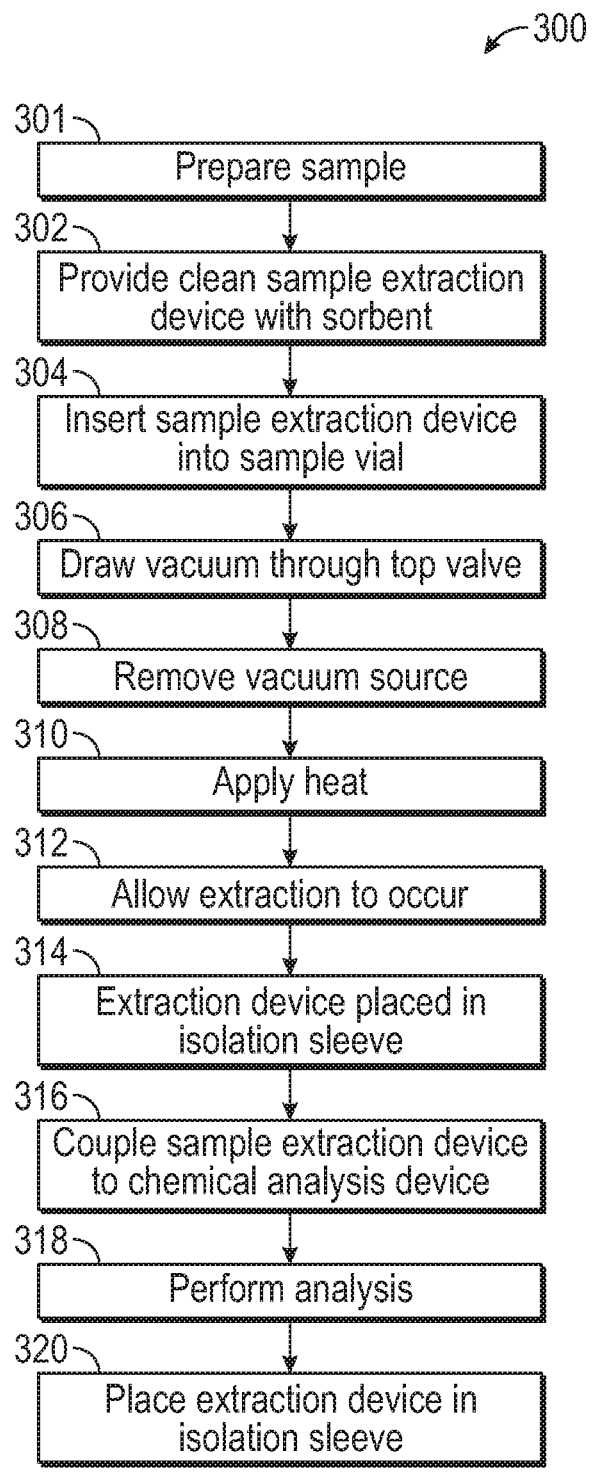
FIG. 3 illustrates an exemplary process for collecting a sample and conducting chemical analysis of the sample according to examples of the disclosure.

FIG. 3 illustrates an exemplary process 300 for collecting a sample and conducting chemical analysis of the sample according to examples of the disclosure. In some examples, in step 301 of process 300, the sample can be prepared. Preparing the sample can include weighing the sample into the sample vial (e.g., sample vial 250) and placing an appropriate cap and lid on the sample vial to allow insertion of a sample extraction device (e.g., sample extraction device 100, 200, or 210) into the sample vial, for example. In some examples, in step 302, the clean sample extraction device can be provided with a sorbent (e.g., sorbent 202).

Next, in step 304, the sample extraction device can be inserted into and coupled to a sample vial (e.g., sample vial 250) that includes a sample (e.g., sample 252), allowing the sample to be extracted from the sample vial into the sample extraction device. The sample extraction device can be sealed to the sample vial by an external seal (e.g., external seal 208) of the sample extraction device, for example. In some examples, in step 306, a vacuum can be drawn in the sample vial through a valve (e.g., sealing plunger 204), and thus via internal channel (e.g., internal channel 230) and lower cavity (e.g., lower cavity 220)—which can include a sorbent (e.g., sorbent 202)—of the sample extraction device. To draw the vacuum, a vacuum source can be coupled to the top (e.g., valve end 214) of the sample extraction device, for example. Next, in step 308, after enough time has passed to create a vacuum in the sample vial, the vacuum source can be removed. In some examples, during step 308, even after sufficient vacuum is reached, the vacuum source can remain coupled to sample extraction device and evacuation of the sample vial can continue for a period of time to boil off some of the matrix in the sample (e.g., water or alcohol). After the vacuum source is removed, the vacuum can be held by the sample extraction device (e.g., using internal seal 206 and external seals 208). In some examples, in step 310, heat can be applied to the sample vial (e.g., in some examples, anywhere from 4 degrees Celsius to 150 degrees Celsius, and typically 25 degrees Celsius).

In some examples, steps 304 and/or 306 can be skipped; for example, rather than being coupled to a sample vial, the sample extraction device can collect a sample from the surrounding air (e.g., the air in the environment of the sample extraction device); in some examples, the sample extraction device can be coupled to the sample vial and sample can be collected at atmospheric pressure in the sample vial—that is, step 306 can be skipped. In some cases of air analysis for indoor or outdoor air monitoring, the sample extraction device can collect sample for up to two weeks to determine an average concentration of chemicals in the air.

Once the extraction process has been set up (e.g., by applying a vacuum and/or heat, or by exposing the sample extraction device to air to be sampled), extraction can be allowed to occur in step 312. In some examples, the sample vial can remain under vacuum and applied heat for a predetermined amount of time, or until "exhaustive extraction" occurs. For example, the process can remain at step 312 for anywhere from one minute to two days depending on the compounds to be analyzed. After the sample is collected in the sample extraction device, the sample extraction device can be placed in an isolation sleeve at step 314 to prevent contamination of the sample during storage. Later, at step 316, the sample extraction device can be coupled to a chemical analysis device (e.g., chemical analysis device 160). At step 318, fluid can be flowed through the sample extraction device, including through the lower cavity of the sample extraction device, which includes the collected sample and a sorbent, to facilitate desorption of the sample into the chemical analysis device, which can perform GC, GCMS, LC, LCMS, or some other analysis procedure to evaluate one or more characteristics of the sample, such as its composition. After chemical analysis is complete, the sample extraction device can be placed in an isolation sleeve at step 320 so that it remains clean until the next extraction.

Figure 4:
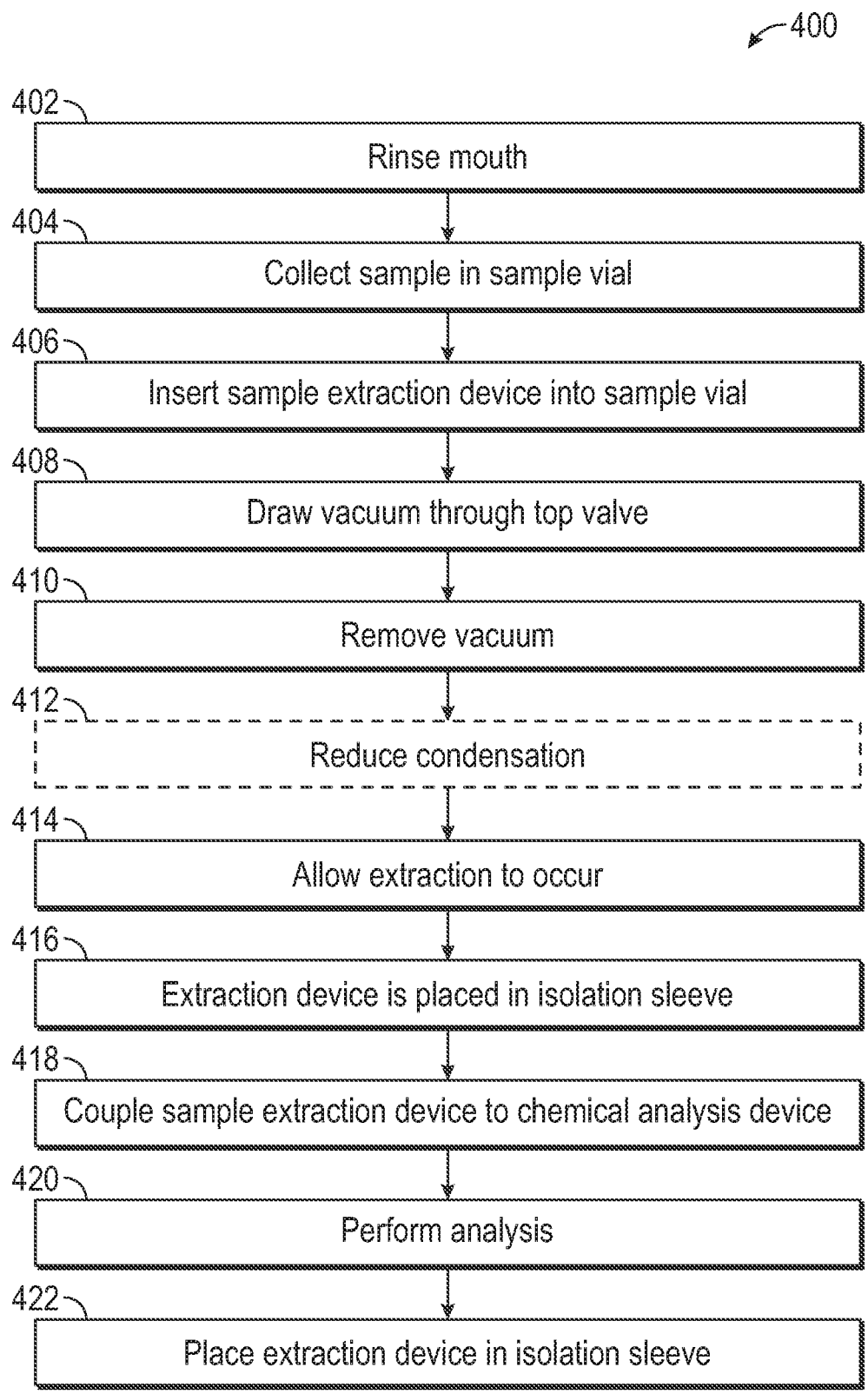
FIG. 4 illustrates an exemplary process for collecting a human breath condensate and/or saliva sample and conducting chemical analysis of the sample according to examples of the disclosure.

In some examples, a sample extraction device according to examples of the disclosure can be used to analyze human breath condensate and saliva to, among other things, recover metabolites for disease screening, detect drugs of abuse, detect chemicals or "biomarkers", and/or generally determine environmental contaminants including endocrine disrupters that could be linked to autism and other conditions. FIG. 4 illustrates an exemplary process 400 for collecting a human breath condensate and/or saliva sample and conducting chemical analysis of the sample according to examples of the disclosure. In some examples, process 400 can improve one or more of sensitivity, ease of operation, recovery of heavier chemicals, the ability to completely eliminate interfering matrix compounds, and can reduce cross-contamination and/or carryover compared to other methods of analyzing human breath condensate and saliva. Because most compounds of interest in human breath can saturate the entire airway in both the nose and mouth, and thus will substantially enrich in saliva and the soft tissues of the mouth, performing an oral rinse with purified water or some other inert liquid can recover these compounds, for example. Then, the volatile and semi volatile organic chemicals (VOCs and SVOCs) can be extracted from the rinse sample.

Specifically, in some examples, in step 402, the subject (e.g., a person) can rinse their mouth with purified water or another inert liquid. A volume of liquid on the order of 10 to 30 mL can be used and the mouth can be rinsed for 5 to 10 seconds, for example. That is to say, in the examples described with reference to FIGS. 1-3, the sample 252 can be the oral rinse deposited by the subject. In step 404, the sample can be collected by depositing the rinse in a sample vial (e.g., sample vial 250) having a volume of 40 mL or more, for example. In some examples, other volumes are possible. The sample vial can be used to transport the sample to a lab for further analysis, for example. At step 406, the sample vial holding the sample can be coupled to the sample extraction device (e.g., sample extraction device 100, 200, or 210) by inserting the sample extraction device into the sample vial, for example. In some examples, the clean sample extraction device can be provided with a sorbent (e.g., sorbent 202). The sample extraction device can be sealed to the sample vial by an external seal (e.g., external seal 208) of the sample extraction device, for example.

At step 408, a vacuum can be drawn in the sample vial through a valve (e.g., sealing plunger 204), and thus via internal channel (e.g., internal channel 230) and lower cavity (e.g., lower cavity 220)—which can include a sorbent (e.g., sorbent 202)—of the sample extraction device. To draw the vacuum, a vacuum source can be coupled to the top (e.g., valve end 214) of the sample extraction device, for example. In some examples, the vacuum can be drawn for a duration of 10 to 20 seconds, though other durations are possible. Next, at step 410 the vacuum source can be removed, though the vacuum can remain in the vial (e.g., using internal seal 206 and external seals 208), greatly increasing the rate of transfer of both volatile and low-volatility chemicals from the liquid sample to the sorbent within the sample extraction device.

In some examples, at step 412, measures can be taken to reduce condensation and/or humidity at the sample extraction device. For example, heat can be applied, using a heater or some other heating element, to the sample extraction device to increase its temperature by 5 to 10 degrees Celsius above the temperature of the sample in the sample vial. Additionally or alternatively, in some examples, the sample can be heated and cooled repeatedly through Pulsed Evaporative Condensation Extraction (PECE). Heating the sample can cause an aqueous solution to boil, especially while under the influence of the internal vacuum, thereby enhancing recovery of low volatility compounds, for example. Recooling the sample can allow the return of the full vacuum so the process can be repeated. In some examples, prior to drawing the vacuum through the top valve in step 408, salt can be added to the sample to decrease water condensation and/or humidity within the sample vial, which can eliminate the need to heat the sample extraction device (e.g., sample extraction device heating can be omitted). In some examples, a final cooling of the sample can be performed to draw condensed water back into the liquid or solid phase of the sample to reduce or avoid analyzer interferences. Salt can reduce the affinity of many organic molecules to an aqueous solution, which can drive the equilibrium towards the adsorbent device in the headspace, for example. Additionally or alternatively, in some examples, salt can also be used in the sample as a preservative to prevent sample degradation during transportation and storage.

Over a period of time (e.g., ranging from several (e.g., 3-5) minutes to one to two days), sample extraction can occur in step 414. In some examples, other periods of time are possible. In step 416, the extraction device can be placed in an isolation sleeve for secure storage between extraction and analysis. In some examples, the sample extraction device can be coupled to a chemical analysis device, at step 418, which can perform GC, LC, GCMS, or LCMS in step 420, as described in this disclosure. After chemical analysis is complete, the extraction device can be placed in the isolation sleeve in step 422 for storage between uses. In some examples, the steps of process 400 can be performed in any order and process 400 may include one or more steps of process 300 described above with reference to FIG. 3.

The above-described method 400 can be used to identify chemical or "biomarkers" for determining conditions of the human body such that a medical professional can diagnose various conditions or diseases. In some examples, inconsistencies in concentrations from one mouth rinse sampling may not cause inaccurate analytical determinations if ratios of certain markers are monitored. If, for example, two markers A and B are of a similar volatility and have an A/B ratio of 3:1 in a healthy person and an A/B ratio of 1:3 in an unhealthy person with a specific disease or condition, the A/B ratio can be determined and used for diagnosis even when the total concentration of breath condensate and/or saliva can vary from test to test. Drugs of abuse will also be present in breath condensate and saliva, along with their metabolic breakdown products. A simple swish and deposit into a vial will show whether someone has been using illegal drugs, or has even been in a drug producing lab due to the presence of unique chemicals found therein. Exposure to other dangerous chemicals can also be evaluated, such as chemical warfare agents, pesticides, phthalates, or endocrine disruptors and xenohormones. Many researchers are looking to a series of such endocrine disrupters as the cause of autism, and method 400 would make it easier for them to detect the levels of such disruptors within affected children and pregnant women. In addition to measuring chemical in an oral rinse, method 400 can be used to measure chemicals in a wide variety of matrices, including pesticides in vegetables, and phthalates in wine and other alcoholic beverages, to name a few. By performing a liquid extraction off of the adsorbent in the sample extraction device, as described previously in this disclosure, analysis by LCMS rather than GCMS can also be performed.

As such, the examples of the disclosure provide an improved sample extraction device and method for extracting sample from, for example, a liquid or solid contained in a sample vial, and desorbing such sample into a chemical analysis device for analysis.

Therefore, according to the above, some examples of the disclosure are related to a cavity configured to contain a sorbent, the cavity having an opening at an extraction end of the sample extraction device; and an internal seal configured to selectively restrict fluid flow through the cavity, the internal seal disposed at a valve end of the sample extraction device. Additionally or alternatively, in some examples, the sorbent is disposed within the cavity such that it is closer to the opening at the extraction end of the sample extraction device than it is to a valve end of the cavity. Additionally or alternatively, in some examples, the sample extraction device further comprises an external seal disposed around an outside of the sample extraction device. Additionally or alternatively, in some examples, the external seal comprises a fluoroelastomer seal or a perfluoroelastomer seal. Additionally or alternatively, in some examples, the external seal is configured to form a seal between the sample extraction device and a sample vial into which the sample extraction device is inserted. Additionally or alternatively, in some examples, the internal seal is configured to facilitate pulling vacuum in the sample vial through the cavity and the sorbent, the vacuum pulled by a vacuum source coupled to the sample extraction device at the valve end. Additionally or alternatively, in some examples, the internal seal is configured to facilitate pulling headspace gas that is inside the sample vial into the cavity and the sorbent. Additionally or alternatively, in some examples, the external seal is disposed at a location on the sample extraction device such that, when the sample extraction device is inserted into the sample vial, the extraction end of the sample extraction device is inside a headspace gas in the sample vial. Additionally or alternatively, in some examples, the internal seal maintains a vacuum inside the sample vial after removal of the vacuum source from the sample extraction device. Additionally or alternatively, in some examples, the external seal is configured to form a seal between the sample extraction device and a chemical analysis device into which the sample extraction device is inserted. Additionally or alternatively, in some examples, the internal seal is configured to facilitate flowing fluid through the cavity and the sorbent and into the chemical analysis device. Additionally or alternatively, in some examples, the sample extraction device further comprises a port configured to facilitate flowing fluid through the cavity and the sorbent and into the chemical analysis device. Additionally or alternatively, in some examples, the internal seal is configured to isolate sample, collected in the sorbent, from an environment of the sample extraction device after a sample extraction process. Additionally or alternatively, in some examples, the cavity is removably coupled to the sample extraction device, and the cavity further comprises one or more sorbent retention devices configured to retain the sorbent within the cavity.

Some examples of the disclosure are related to a method comprising coupling a sample vial to a sample extraction device via an external seal of the sample extraction device, wherein the sample vial includes a sample and a headspace gas, the sample comprising one or more of a solid and a liquid; drawing a vacuum in the sample vial through an internal seal of the sample extraction device, such that in the process of drawing the vacuum, the headspace gas is drawn through a sorbent included in the sample extraction device; and collecting the sample in the sorbent included in the sample extraction device while the vacuum is drawn in the sample vial.

Some examples of the disclosure are related to a method comprising coupling a sample vial to a sample extraction device via an external seal of the sample extraction device, wherein the sample vial includes a sample, the sample comprising one or more of a solid and a liquid; coupling a vacuum source to the sample extraction device; drawing a vacuum, with the vacuum source, in the sample vial through an internal seal of the sample extraction device for a first period of time, such that in the process of drawing the vacuum, the vacuum is drawn through a sorbent included in the sample extraction device; removing the vacuum source after the vacuum is drawn; after removing the vacuum source, collecting the sample in the sorbent included in the sample extraction device, for a second period of time, while the vacuum is held in the sample vial. Additionally or alternatively, in some examples, the method further includes after collecting the sample, decoupling the sample extraction device from the sample vial; coupling the sample extraction device to a column of a chemical analysis device; and passing a carrier fluid through a port on the sample extraction device seal and the sorbent of the sample extraction device and into the column of the chemical analysis device. Additionally or alternatively, in some examples, the chemical analysis device is configured to perform one or more of gas chromatography, gas chromatography-mass spectrometry, liquid chromatography, and liquid chromatography-mass spectrometry on the sample. Additionally or alternatively, in some examples, the method further includes after decoupling the sample extraction device from the sample vial and prior to coupling the sample extraction device to the column of the chemical analysis device and passing the carrier fluid through the internal seal of the sample extraction device: sealing the sample extraction device; an storing the sample extraction device. Additionally or alternatively, in some examples, the method further includes one or more of adsorbing and absorbing the sample into the sorbent while collecting the sample in the sorbent. Additionally or alternatively, in some examples, the method further includes eluting the sample from the sorbent using a solvent to form an extract; and inserting the extract into a chemical analysis device to perform one or more of gas chromatography, gas chromatography-mass spectrometry, liquid chromatography, and liquid chromatography-mass spectrometry on the extract. Additionally or alternatively, in some examples, the first period of time lasts until one or more of water and alcohol are eliminated from the sample. Additionally or alternatively, in some examples, the second period of time lasts until sufficient extraction of the liquid or solid sample has occurred, until equilibrium between the sample extraction device and the contents of the sample vial has been achieved, or until complete extraction of GC or LC compatible compounds from the sample in the sample vial has been achieved.

Some examples of the disclosure are related to a method comprising: preparing a sample by rinsing a mouth of a subject with an inert liquid to combine the inert liquid with one or more of saliva and breath condensate; and depositing the combination of the inert liquid and the one or more of the saliva and breath condensate into a sample vial; extracting, from the combination of the inert liquid and the one or more of the saliva and breath condensate, the sample from the sample vial; and performing a chemical analysis of the sample. Additionally or alternatively, in some examples, extracting the sample from the sample vial comprises: coupling the sample vial to a sample extraction device via an external seal of the sample extraction device, wherein the sample vial includes the sample, the sample comprising the combination of the inert liquid and the one or more of the saliva and breath condensate into a sample vial; coupling a vacuum source to the sample extraction device; drawing a vacuum, with the vacuum source, in the sample vial through an internal seal of the sample extraction device for a first period of time, such that in the process of drawing the vacuum, the vacuum is drawn through a sorbent included in the sample extraction device; removing the vacuum source after the vacuum is drawn; and after removing the vacuum source, collecting the sample in the sorbent included in the sample extraction device, for a second period of time, while the vacuum is held in the sample vial. Additionally or alternatively, in some examples, performing the chemical analysis of the sample comprises: after collecting the sample, decoupling the sample extraction device from the sample vial; coupling the sample extraction device to a column of a chemical analysis device; and passing a carrier fluid through a port on the sample extraction device and the sorbent of the sample extraction device and into the column of the chemical analysis device. Additionally or alternatively, in some examples, the chemical analysis device is configured to perform one or more of gas chromatography, gas chromatography-mass spectrometry, liquid chromatography, and liquid chromatography-mass spectrometry on the sample. Additionally or alternatively, in some examples, the method further comprises after decoupling the sample extraction device from the sample vial and prior to coupling the sample extraction device to the column of the chemical analysis device and passing the carrier fluid through the internal seal of the sample extraction device: sealing the sample extraction device; and storing the sample extraction device. Additionally or alternatively, in some examples, the method further comprises one or more of adsorbing and absorbing the sample into the sorbent while collecting the sample in the sorbent. Additionally or alternatively, in some examples, the method further comprises eluting the sample from the sorbent using a solvent to form an extract; and inserting the extract into a chemical analysis device to perform one or more of gas chromatography, gas chromatography-mass spectrometry, liquid chromatography, and liquid chromatography-mass spectrometry on the extract. Additionally or alternatively, in some examples, the first period of time lasts until water is eliminated from the sample. Additionally or alternatively, in some examples, the first period of time is in the range of 10-20 seconds. Additionally or alternatively, in some examples, the second period of time lasts until a desired amount of extraction of the sample has occurred, until equilibrium between the sample extraction device and an inside of the sample vial has been achieved, or until complete extraction of one or more given compounds from the sample in the sample vial has been achieved. Additionally or alternatively, in some examples, the second period of time lasts one to two days. Additionally or alternatively, in some examples, the second period of time lasts three to five minutes. Additionally or alternatively, in some examples, extracting the sample from the sample vial further comprises: while the vacuum is held in the sample vial, heating the sample extraction device to increase a temperature of the sample extraction device to a temperature that is greater than a temperature of the sample by an amount in the range of 5 to 10 degrees Celsius. Additionally or alternatively, in some examples, the method further comprises prior to coupling the vacuum source to the sample extraction device, depositing a salt into the sample vial. Additionally or alternatively, in some examples, the inert liquid is purified water. Additionally or alternatively, in some examples, the chemical analysis of the sample indicates one or more chemical compounds included in the one or more of the saliva and breath condensate. Additionally or alternatively, in some examples, the volume of the inert liquid is between 10 and 100 cc. Additionally or alternatively, in some examples, the method further includes performing a sequence of heating the sample extraction device followed by cooling the sample extraction device one or more times; and drawing condensed water included in the sample vial into the liquid or solid phase of the combination of the inert liquid and the one or more of the saliva and breath condensate. Additionally or alternatively, in some examples, the method further comprises calculating a ratio of marker compounds based on the chemical analysis of the sample.

Some examples of the disclosure are directed to a system comprising: a sample extraction device; a sample vial containing a sample, the sample prepared in a method comprising rinsing a mouth of a subject with an inert liquid to combine the inert liquid with one or more of saliva and breath condensate; and depositing the combination of the inert liquid and the one or more of the saliva and breath condensate into the sample vial, and a chemical analysis device configured to perform a chemical analysis of the sample. Additionally or alternatively, in some examples, the sample vial has a volume greater than 10 cc. Additionally or alternatively, in some examples, the system further comprises a heating element configured to heat the sample vial to a temperature that is greater than a temperature of the sample by 5 to 10 degrees Celsius. Additionally or alternatively, in some examples, the system further includes a cooling element configured to cool the sample extraction device.

Although examples have been fully described with reference to the accompanying drawings, it is to be noted that various changes and modifications will become apparent to those skilled in the art. Such changes and modifications are to be understood as being included within the scope of examples of this disclosure as defined by the appended claims.

The invention claimed is:

1. A method comprising:
preparing a sample by:
rinsing a mouth of a subject with an inert liquid to combine an inert liquid with one or more of saliva and breath condensate; and
depositing the combination of the inert liquid and the one or more of the saliva and breath condensate into a sample vial;
coupling a sample extraction device to the sample vial, wherein coupling the sample extraction device to the sample vial seals the sample vial from an environment of the sample vial, and the sample extraction device includes a sorbent;
coupling a vacuum source to the sample extraction device;
drawing a vacuum, with the vacuum source, in the sample vial through the sample extraction device for a first period of time, such that in the process of drawing the vacuum, the vacuum is drawn through the sorbent included in the sample extraction device;
ceasing to draw the vacuum in the sample vial;
after ceasing to draw the vacuum in the sample vial and while the vacuum is held in the sample vial, extracting, from the combination of the inert liquid and the one or more of the saliva and breath condensate, one or more volatile or semi-volatile compounds of the sample from the sample vial; and
collecting the one or more volatile or semi-volatile compounds of the sample in the sorbent of the sample extraction device; and
performing a chemical analysis of the one or more volatile or semi-volatile compounds of the sample.

2. The method of claim 1, wherein performing the chemical analysis of the sample comprises:
after collecting the sample, decoupling the sample extraction device from the sample vial;
coupling the sample extraction device to a column of a chemical analysis device; and
passing a carrier fluid through a port on the sample extraction device and the sorbent of the sample extraction device and into the column of the chemical analysis device.

3. The method of claim 1, further comprising:
eluting the sample from the sorbent using a solvent to form an extract; and
inserting the extract into a chemical analysis device to perform one or more of gas chromatography, gas chromatography-mass spectrometry, liquid chromatography, and liquid chromatography-mass spectrometry on the extract.

4. The method of claim 1, wherein drawing the vacuum occurs for a period of time in the range of 10-20 seconds.

5. The method of claim 1, wherein collecting the one or more volatile or semi-volatile compounds occurs until equilibrium between the sample extraction device and an inside of the sample vial has been achieved.

6. The method of claim 1, wherein collecting the one or more volatile or semi-volatile compounds occurs for a period of time of one to two days.

7. The method of claim 1, wherein collecting the one or more volatile or semi-volatile compounds occurs for a period of time lasting three to five minutes.

8. The method of claim 1, wherein extracting the sample from the sample vial further comprises:
while the vacuum is held in the sample vial:
heating the sample extraction device to increase a temperature of the sample extraction device to a temperature that is greater than a temperature of the sample by an amount in the range of 5 to 10 degrees Celsius; and
reducing or preventing water condensation on the sorbent.

9. The method of claim 1, further comprising:
prior to coupling the vacuum source to the sample extraction device, depositing a salt into the sample vial.

10. The method of claim 1, wherein the inert liquid is purified water.

11. The method of claim 1, wherein the chemical analysis of the sample indicates the one or more volatile or semi-volatile compounds included in the one or more of the saliva and breath condensate.

12. The method of claim 1, further comprising calculating a ratio of marker compounds based on the chemical analysis of the sample.

13. The method of claim 1, wherein the volume of the inert liquid is between 10 and 100 cc.

14. The method of claim 1, wherein preparing the sample occurs at a first location and performing the chemical analysis occurs at a second location different from the first location, and the method further comprises:
transporting the sample within the sample extraction device from the first location to the second location.

15. The method of claim 1, wherein the sorbent included in the sample extraction device is placed in a headspace of the sample vial at a position that does not touch a liquid phase of the inert liquid and the one or more of the saliva and breath condensate in the sample vial while collecting the one or more volatile or semi-volatile compounds of the sample in the sorbent of the sample extraction device.

16. The method of claim 1, wherein after ceasing to draw the vacuum in the sample vial and while the vacuum is held in the sample vial, an inside of the sample vial is a closed system.

17. A system comprising:
a sample extraction device including a sorbent;
a sample vial containing a sample, the sample prepared in a method comprising:
rinsing a mouth of a subject with an inert liquid to combine the inert liquid with one or more of saliva and breath condensate; and
depositing the combination of the inert liquid and the one or more of the saliva and breath condensate into the sample vial;
coupling a sample extraction device to the sample vial, wherein coupling the sample extraction device to the sample vial seals the sample vial from an environment of the sample vial, and the sample extraction device includes a sorbent;
coupling a vacuum source to the sample extraction device;
drawing a vacuum, with the vacuum source, in the sample vial through the sample extraction device for a first period of time, such that in the process of drawing the vacuum, the vacuum is drawn through the sorbent included in the sample extraction device;
cease drawing the vacuum in the sample vial;
after ceasing to draw the vacuum in the sample vial and while the vacuum is held in the sample vial, extracting, from the combination of the inert liquid and the one or more of the saliva and breath condensate, one or more volatile or semi-volatile compounds of the sample from the sample vial; and
collecting the one or more volatile or semi-volatile compounds of the sample in the sorbent of the sample extraction device, and
a chemical analysis device configured to perform a chemical analysis of the one or more volatile or semi-volatile compounds of the sample.

18. The system of claim 17, further comprising a heating element configured to heat the sample extraction device to a temperature that is greater than a temperature of the sample by 5 to 10 degrees Celsius.

19. The system of claim 17, further comprising a cooling element configured to cool the sample extraction device.

* * * * *